US006488978B2

(12) United States Patent
Sasaki et al.

(10) Patent No.: US 6,488,978 B2
(45) Date of Patent: Dec. 3, 2002

(54) ANTI-BACTERIA AGENT MADE FROM SHELL, AND METHODS FOR PURIFYING AND DESALINATING WATER AND FOR WASHING AGRICULTURAL PRODUCTS WITH USE THEREOF

(75) Inventors: Keiko Sasaki, Miyagi (JP); Manabu Sasaki, Miyagi (JP); Yukio Funai, Tokyo (JP); Kasumi Koyama, Tokyo (JP)

(73) Assignee: Surfcera Co., Ltd., Tokyo (JP)

( * ) Notice: Subject to any disclaimer, the term of this patent is extended or adjusted under 35 U.S.C. 154(b) by 0 days.

(21) Appl. No.: 09/885,682

(22) Filed: Jun. 20, 2001

(65) Prior Publication Data

US 2002/0009499 A1 Jan. 24, 2002

Related U.S. Application Data

(62) Division of application No. 09/515,226, filed on Feb. 29, 2000, now Pat. No. 6,365,193.

(30) Foreign Application Priority Data

Aug. 30, 1999 (JP) ............................................. 11-242755

(51) Int. Cl.$^7$ ...................... A23C 3/3472; A01N 65/00; A61K 35/42; A23L 3/34
(52) U.S. Cl. ........................................ 426/532; 424/538
(58) Field of Search ................................. 426/520, 532; 424/538

(56) References Cited

U.S. PATENT DOCUMENTS

| 4,808,330 A | * | 2/1989 | Chung ........................ 426/532 |
| 5,409,714 A | * | 4/1995 | Ishijima et al. ............. 426/532 |
| 5,674,538 A | * | 10/1997 | Lokkesmoe et al. ........ 426/532 |
| 5,683,724 A | * | 11/1997 | Hei et al. .................... 426/532 |
| 5,855,940 A | * | 1/1999 | Compadre et al. .......... 426/532 |
| 5,858,435 A | * | 1/1999 | Gallo ........................... 426/532 |

FOREIGN PATENT DOCUMENTS

| JP | 60-126207 | 7/1985 |
| JP | 61-28494 | 2/1986 |
| JP | 4-333711 | 11/1992 |
| JP | 9-77907 | 3/1997 |
| JP | 9-103234 | 4/1997 |
| JP | 9-315901 | 12/1997 |
| JP | 9-324180 | 12/1997 |
| JP | 10-137738 | 5/1998 |
| JP | 11-29424 | 2/1999 |
| JP | 11-50391 | 2/1999 |
| JP | 2000-72610 | 3/2000 |

* cited by examiner

*Primary Examiner*—Herbert J. Lilling
(74) *Attorney, Agent, or Firm*—Merchant & Gould P.C.

(57) ABSTRACT

For providing an anti-bacteria which is made from a natural material, therefore harmless if it is absorbed in the human body, can be produced in mass production with low cost, and shows a high anti-bacteria effect, the anti-bacteria agent is obtained by heating a shell in an atmosphere of inactive gas and burning the shell under the temperature which finally reaches 700° C.–2,500° C.

8 Claims, 3 Drawing Sheets

Figure 1:
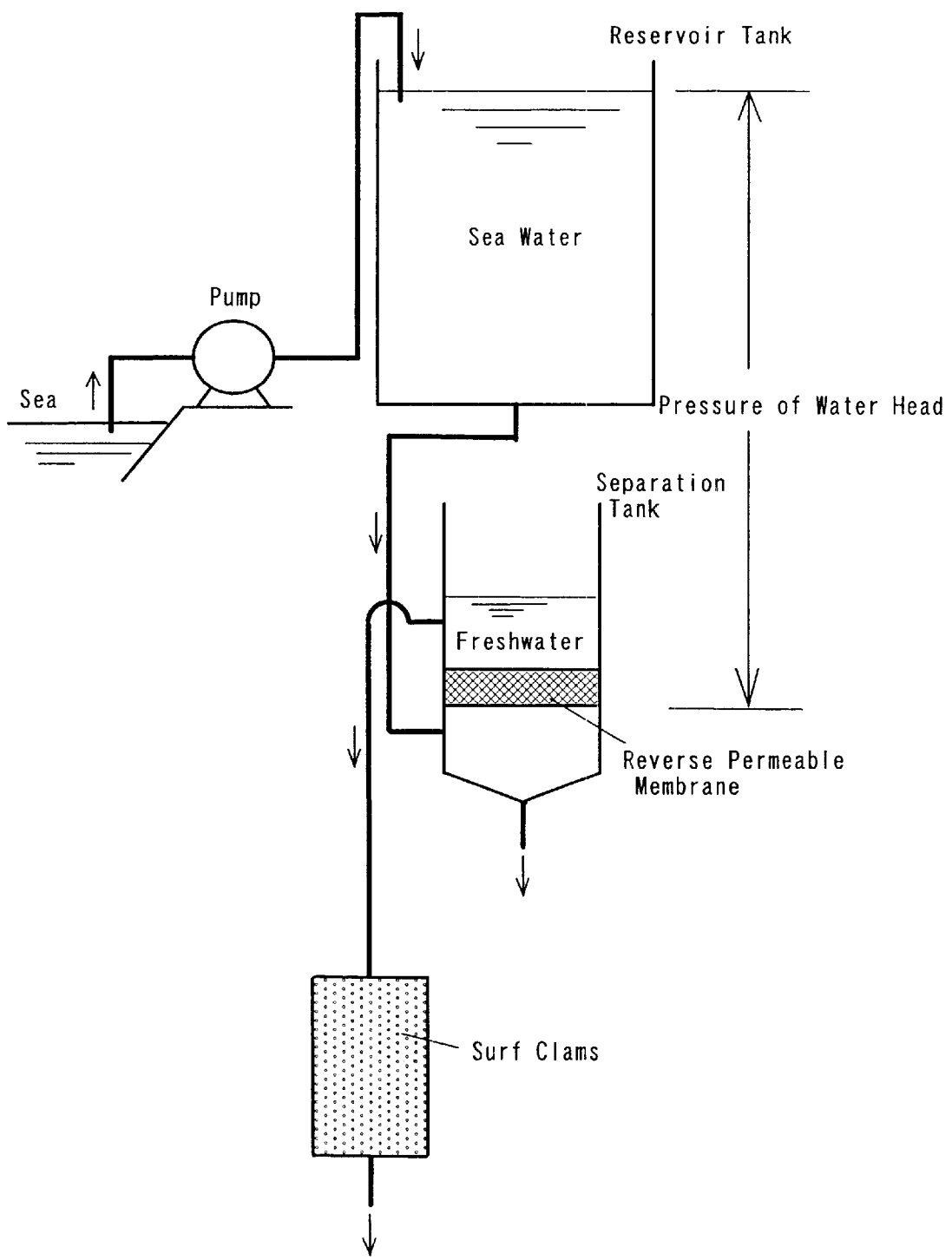

ANTI-BACTERIA AGENT MADE FROM SHELL, AND METHODS FOR PURIFYING AND DESALINATING WATER AND FOR WASHING AGRICULTURAL PRODUCTS WITH USE THEREOF

This application is a divisional of application Ser. No. 09/515,226, filed Feb. 29, 2000 now U.S. Pat. No. 6,365,193, which application(s) are incorporated herein by reference.

BACKGROUND OF THE INVENTION

1. Field of the Invention

The present invention relates to an anti-bacteria agent which is suitable for protecting foods from contamination with bacteria, in processed foods manufacturing industry, in food restaurant industry, and at home, and for disinfecting, sterilizing or pasteurizing in medical industry and medical welfare industry, and relates to a method for desalinating and purifying sea water and river water, and further to a method for washing or cleaning with use of water purified this anti-bacteria agent.

2. Description of Prior Art

Chemical compound(s) of chlorine was used as a general anti-bacteria agent. However, it sometimes generated trihalomethane in a treatment of waste water and/or generated dioxin in an incinerating or burning treatment. As examples of anti-bacteria agents, which have been used as a food additive in farming and fisheries or marine products industry, there are synthetic anti-bacteria agent, such as sulfamizin, carbadox, or the like, as medicines for animals. However they must be strictly controlled, in particular, in residual value thereof to be less than a standard value, from a view point of safety of foods.

Therefore, the anti-bacteria agents made from natural materials as ingredients, rather than the anti-bacteria agents of chemical compound(s) mentioned above are required, in particular, in a field of treating foods which has a possibility to be taken inside the human body through a mouth. For example, a report "An Effect of Green Tea On O-157" was published by the group of Prof. TeLdakatsu Shimamura, the medical department of Showa University, and attracted attention of many consumers. After this publication, catechin of tea, though it was conventionally used as a food additive, has come into wide use.

The catechin of tea, attracting attention as an anti-bacteria agent made from a natural material, must be extracted from green tea as an ingredient, therefore is not suitable for mass production. Accordingly, a new anti-bacteria agent is required, which is made from a natural material as an ingredient, is harmless when absorbed in the human body, can be produced in mass production with low cost, and shows a further high anti-bacteria effect.

In particular, an anti-bacteria agent which is made from a natural material and is harmless when absorbed into the human body, is considered also to have an effect on purification of water. Hereinafter, there are listed examples or cases now in issues.

First, the desalination of sea water can be listed. In the countries of the Middle East, freshwater is obtained from sea water through a reverse permeable membrane method, a distillation method, a refrigeration method or an electric dialysis method, etc., in general. When salt etc., is removed from sea water in this manner, bacteria can easily propagate. Therefore an anti-bacteria agent of Cr group or Cl group, is added to prevent the propagation of bacteria. However, the agent of the Cr group or Cl group is extremely harmful to the human body, and a danger of producing cancer cannot be denied.

Second, the purification of river water can be listed. In river water into which drainage by human life (organic matter) flows, the BOD value is high, and it generates bad smell.

Third, washing or rinsing of agricultural products can be listed. To agricultural products after a harvest, an insecticide sometimes adheres. As a result of this, after agricultural products are washed with a synthetic detergent, they are rinsed with water for general use (i.e., water from a water supply or from rivers), in order to wash such insecticide away. However, since ordinary water is poor in anti-bacteria effect or power by itself, there is a possibility that bacteria propagates on the surface of agricultural products until they reach general consumers.

SUMMARY OF THE INVENTION

For dissolving the problems mentioned above, according to the claim 1 of the present invention, there is provided an anti-bacteria agent made from shell. An anti-bacteria agent, according to the present invention, is obtained by heating a shell in an atmosphere of inactive gas and burning the shell under the temperature which finally reaches 700° C.–2,500° C.

As shells, a surf clam is the most preferable, since it is recognized to have sterilizing power against general bacteria. However it may be any one of an oyster, a scallop, a clam, a turban shell and a snail, if it is burned. By burning, the shell itself comes to be porous, therefore a contacting area is increased, thereby remarkably improving sterilizing or disinfecting power.

In particular, a shell powder of a surf clam, by burning in an atmosphere of inactive gas, shows strong and continuous property of anti-bacteria against germs or bacteria, such as *Escherichia coli* O-157 or the like, even if it is added only a little bit. It is also a natural materiel which mainly contains calcium, therefore it is safe for the human body. In addition, in a case where it is disposed, it never contaminates air, water, or soil. It also brings an effect that shells, which were too much to be managed as waste conventionally, can be utilized effectively.

If the anti-bacteria agent mentioned above is crushed to have a maximum particle diameter equal to or less than 100 $\mu$m and have a mean particle diameter from 1 $\mu$m to 50 $\mu$m, it can be easily dissolved into water (in particular, into warm water), thereby enabling to further improve its anti-bacterial effect.

The burned shells made from natural material or natural ingredient are described in No. 218 of the list of the existing additives, which is defined in the revised version of the Food Hygiene Act and the Nutrition Improvement Act as burned calcium (which mainly contains calcium compounds obtained by burning shells or the like). It is officially recognized to be safe for the human body.

Accordingly, regarding the anti-bacteria agent according to the present invention, it is preferable to be used for protecting foods from contamination by germs or bacteria in food service or food restaurant industry or at home, and for sterilization, pasteurization, or disinfection in medical industry or medical welfare industry.

The anti-bacteria agent of the present invention, which is applied to desalination, is made be contact with freshwater obtained from sea water by using any one of the reverse permeable membrane method, the distillation method, the refrigeration method or the electric dialysis method.

As a result of such structure, it is possible to remove or remarkably reduce the amount of a disinfectant or germicide of the Cr group or Cl group added to freshwater after obtained from sea water.

According to the present invention, which is applied to purification of river water, the above-mentioned anti-bacteria agent is filled into a net (including a case through which river water permeates), and the net is provided to be laid within a river.

The burned shells, in addition to the anti-bacteria function of itself, come to be porous, therefore bacteria which decomposes organic matter propagates on the surface thereof, thereby promoting purification of river water. Further, if river water is increased in a degree of an acidity thereof, the burned shells are dissolved into river water, so as to maintain a pH value within the most suitable range.

According to the present invention, which is applied to washing of agricultural products, agricultural products such as vegetables, fruits or the like are rinsed with water contacted with the above-mentioned anti-bacteria agent after washed with synthetic detergent.

As a result of this structure, it is possible to suppress propagation of germs or bacteria on the surface of such agricultural products for a long time period.

BRIEF DESCRIPTION OF THE DRAWING(S)

Figure 2A:
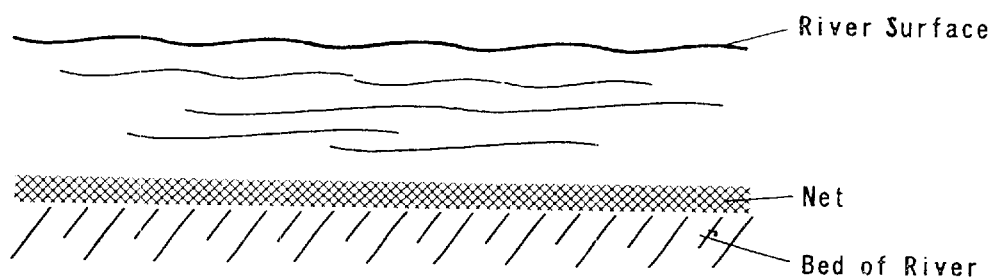
Figure 2B:
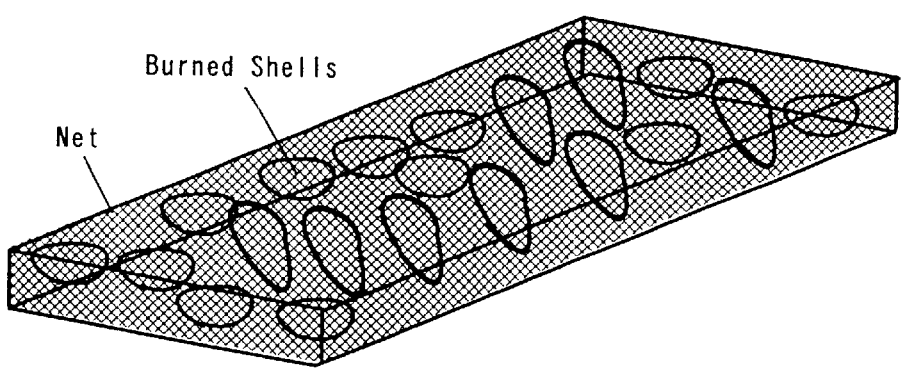
Figure 3A:
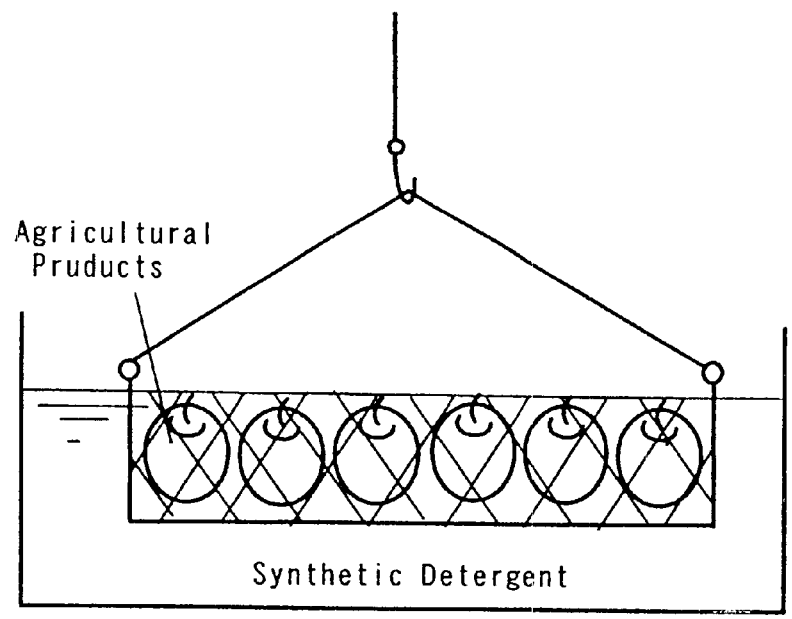
Figure 3B:
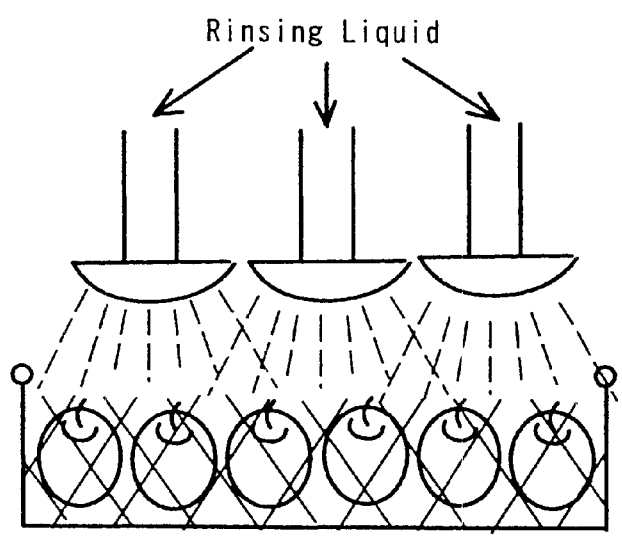

FIG. 1 is a block diagram showing desalination processes for obtaining freshwater from sea water;

FIGS. 2 (A) and (B) show a view explaining a purification method of river water and a perspective view of a net which is provided to be laid on river floor respectively; and FIGS. 3 (A) and (B) are views showing a condition of washing agricultural products and a condition of rinsing after the washing.

DETAILED DESCRIPTION OF PREFERRED EMBODIMENT(S)

Hereinafter, embodiments according to the present invention will be fully explained by referring to the attached drawings.

A surf clam, as an ingredient or raw material of the anti-bacteria agent according to the present invention, is a kind of bivalves, and it is distributed in the seas around the middle part of the main island of Japan and in the northern part of the Sea of Japan. This surf clam is served or used as a canned food, or a frozen or fresh food; however the shell of this is not used effectively. Therefore, the cost for supplying is low.

To manufacture the anti-bacteria agent of the present invention from the surf clam, first, the shells of the surf clam are crushed. The shells are dried, and thereafter, they are roughly crushed by means of a grind mill and so on, thereby adjusting to be equal to or less than 5 mm in a maximum diameter thereof.

Next, the crushed shells are entered into an autoclave equipped with a stirrer, and burned under an inactive gas atmosphere while being stirred. The inactive gas is preferably to be nitrogen gas. A method of increasing temperature is not in question; however the final temperature reaches a range from 700° C. to 2,500° C., more preferably, 900° C.±50° C., and the temperature is maintained for three (3) minutes or longer.

If the final temperature is less than 700° C., it is difficult to obtain the anti-bacterial property. If it exceeds 1,000° C., an active portion of the particle is broken or destroyed, therefore it is also impossible to obtain the anti-bacterial property. In addition, if the burning time is less than three (3) minutes, it is difficult to obtain the anti-bacterial property It does not matter if the burning time is long; however it is preferable to be from three (3) minutes to five (5) minutes from a view point of the cost.

Then, the burned shell particles are cooled under the inactive atmosphere, and thereafter they are further finely crushed and classified or divided to be equal to or less than 100 μm in a maximum particle diameter, to be from 1 μm to 50 μm in a mean particle diameter, and more preferably to be powders within a range from 2 μm to 5 μm.

In a case where the maximum diameter of the particles exceeds 100 μm or the mean diameter exceeds a range from 1 μm to 50 μm, they cannot be dissolved into drink water, and they are deposited or settled, therefore it is impossible to show their function. In a case where the mean particle diameter is less than 1 μm, they absorb moisture, so as to be solid. It is difficult to handle.

However, depending upon the condition of use, it is also possible to use the burned shells without crushing. If they are crushed into minute particles, they can be dissolved into water. Therefore the effect is large; however the effect disappears in a short time. To maintain the effect for a long time, it is preferable that the burned shells are used without crushing, or powders crushed into minute particles are mixed together with a binder, and thereafter are burned, thereby forming into a predetermined form.

The anti-bacteria agent manufactured in the manner mentioned above is effective to *Esherichia coli*, such as O-157 or the like, food poisoning bacteria, such as *Staphylococcus aureus, Psedomonas aeruginosa*, Eumycetes, salmonella, enteritis vibrio or the like, and virus.

As a concrete use of the anti-bacteria agent according to the present invention, it can be used as an additive into a food, such as a boiled fish paste (called kamaboko in Japan) or the like, drink water, hand-washing water, and dental materials, such as an artificial tooth or the like. In addition, it can be used to be put into a pot for home use as anti-bacteria powders pack, or to disinfect drink water for disaster or emergency time. It can be used to be added into a sheet which is for cleaning and wiping, a paper diaper, a wall paper, or building materials, as an anti-bacteria function additive. As other methods for use, the anti-bacteria agent itself can be made into a ceramic, or sterilizing apparatus or device can be produced with use of the anti-bacteria function thereof.

The anti-bacterial agent according to the present invention shows a higher anti-bacteria property than that of tea catechin or oyster shell. Therefore, it is characterized that the anti-bacteria effect can be obtained with a little amount, and that the effect is maintained for a long time. For example, an addition amount for drink water or for other objects to be disinfected is sufficient to be 0.025 weight % with respect to the weight of drink water or other objects. An amount more than this may be added depending upon the condition of use. The anti-bacteria effect can be maintained for a long time, and it is confirmed that the effect can be maintained more than 48 hours.

EXAMPLES

Manufacture of Anti-Bacteria Agent:

Shells of surf clams were dried, and thereafter pre-crushed into about 2 mm–3 mm in size. 500 g thereof were put into an autoclave equipped with a stirrer, which was filled with nitrogen gas and had a capacity of 2 liters. A temperature was started to be increased while the stirrer was slowly operated. This was continued until the temperature reached 900° C. After the shells were burned for five (5) minutes at 900° C., the heating was stopped. Then, the shells were left for cooling within the flow of nitrogen gas until the inside of the autoclave turned back to the room temperature.

After being left for cooling, the burned shell powders were taken out from the autoclave, and they were further crushed by means of a mortar. The particles being equal to or less than 50 μm were selected by a selector, thereby manufacturing the anti-bacteria agent according to the present invention.

The ingredient concentration of this anti-bacteria agent is shown on the following Table 1 (by an analysis according to soil nutriment analyzing method made by Yamagata-ken Rikagaku-Bunseki (physics and chemistry analysis) Center: Yama-Bun-Se No. 778).

TABLE 1

| Measured Ingredient | Concentration (wet weight %) | Minimum Value of Dectection |
|---|---|---|
| Magnesium | 0.04 | |
| Phosphor Bronze | 0.02 | |
| Potassium | 0.07 | |
| calcium | 25. | |
| Manganese | 0.01 | |
| Iron | 0.07 | |
| Copper | Not detected | 0.01 |
| Zinc | Not detected | 0.01 |
| Molybdenum | Not detected | 0.01 |

Charcoal of bamboo crushed and adjusted to be particles equal to or less than 50 μm, in the same manner as mentioned above, separately, was mixed with the above-mentioned anti-bacteria agent made from surf clams at a weight ratio 1:1, thereby manufacturing the anti-bacteria agent according to another embodiment.

Further, in place of surf clams, shells of oysters was used to be burned and crushed in the same manner as mentioned above, thereby manufacturing oyster shell powders.

Test Bacteria:

Three kinds, i.e., *Esherichia coli* ATCC 8739, *Staphylococcus aureus* ATCC 6538, and *Psedomonas aeruginosa* ATCC 9027) were used, and cultured, on a culture medium, such as a DD checker for general bacteria of blood agar flat plate, under a culturing condition for 18 hours at 37° C.

Testing Method:

Each of the anti-bacteria agents manufactured was dissolved into distilled water and adjusted to be at a predetermined concentration. Then each of the above-mentioned test bacteria was added to the distilled water into which the anti-bacteria agent was dissolved, so as to be about 106 pieces/ml.

After each bacteria was added, it was well stirred and left still at the room temperature. After a predetermined time, it was sampled to be measured on numbers (pieces/ml) of the cultured bacteria.

Example 1

With use of a distilled-water solution (1 weight %, 0.5 weight %, 0.1 weight %, and 0.05 weight %) of the anti-bacteria agent made from surf clams and manufactured in the manner mentioned above, the disinfecting effects were examined on each of *Esherichia coli, Staphylococcus aureus*, and *Psedomonas aeruginosa*. The result is shown in Table 2.

Example 2

In the same manner as in Example 1 mentioned above, except that the mixed anti-bacteria agent between surf clams and bamboo charcoal (weight ratio: 1:1) was used in place of the anti-bacteria agent made from surf clams, the disinfecting effects of the mixed anti-bacteria agent were examined. The result is also shown in Table 2.

Example 3

In the same manner as in Example 1 mentioned above, except that an anti-bacteria agent made from oyster shells was used in place of the anti-bacteria agent made from surf clams, the disinfecting effects of the anti-bacteria agent were examined. The result is also shown in Table 2.

TABLE 2

| Examples and Comparison | Concentration of Anti-bacteria Agent (W %) | *Esherichia coli* | | *Staphylococcus aureus* | | *Psedomonas aeruginosa* | |
|---|---|---|---|---|---|---|---|
| | | After 15 minutes | After 24 hours | After 15 minutes | After 48 hours | After 15 minutes | After 24 hours |
| Example 1 | 1% | <20 | <20 | <2 | <2 | <2 | <2 |
| | 0.5% | <20 | <20 | — | — | — | — |
| | 0.1% | <20 | <20 | $1.9 \times 10^2$ | 60 | <2 | <2 |
| | 0.05% | <20 | <20 | — | — | — | — |
| Example 2 | 1% | <20 | <20 | $2.0 \times 10^2$ | 80 | <2 | <2 |
| | 0.5% | <20 | <20 | — | — | — | — |
| | 0.1% | <20 | <20 | $2.0 \times 10^4$ | $2.0 \times 10^2$ | <2 | <2 |
| | 0.05% | $4.0 \times 10^3$ | <20 | — | — | — | — |
| Comparison 1 | 1% | <20 | <20 | 40 | 2 | <20 | 2 |
| | 0.5% | $6.4 \times 10^2$ | <20 | — | — | — | — |
| | 0.1% | $2.5 \times 10^3$ | $2.5 \times 10^6$ | $4.0 \times 10^5$ | $5.2 \times 10^5$ | $2.2 \times 10^2$ | <1 |
| | 0.05% | $2.5 \times 10^5$ | $1.2 \times 10^5$ | — | — | — | — |
| Reference: Distilled water | | $6.0 \times 10^5$ | $4.0 \times 10^5$ | $4.0 \times 10^5$ | $3.6 \times 10^5$ | $8.0 \times 10^5$ | $4.0 \times 10^6$ |

As is apparent from the test results shown in Table 2, the anti-bacteria agent made from surf clams achieved a sufficient disinfecting effect even in a low concentration thereof, i.e., 0.05%. The effect was maintained not only after 24 hours, but also after 48 hours. With respect to the oyster anti-bacteria agent, the effect can be obtained in the concentration of 1%. Accordingly, it can be said that surf clam is the most effective.

Example 4

The concentration of the distilled-water solution of the anti-bacteria agent made from surf clams was decreased to be lower than in Example 1 (i.e., 0.025 weight %, and 0.005 weight %), the disinfecting effects were examined on each of *Esherichia coli* and *Staphylococcus aureus*. The result is shown in Table 3.

Example 5

In the same manner as in Example 4 mentioned above, except that the anti-bacteria agent made from oyster shells was used in place of the anti-bacteria agent made from surf clams, the disinfecting effects were examined. The result is also shown in Table 3.

TABLE 3

| Examples and Reference | Concentration of Anti-bacteria Agent (W %) | *Esherichia coli* ($2.0 \times 10^5$) After 1 hours | *Esherichia coli* ($2.0 \times 10^5$) After 24 hours | *Staphylococcus aureus* ($2.0 \times 10^5$) After 1 hours | *Staphylococcus aureus* ($2.0 \times 10^5$) After 48 hours |
|---|---|---|---|---|---|
| Example 3 | 0.025% | 4 | <2 | 20 | <2 |
|  | 0.005% | $1.6 \times 10^5$ | $4.0 \times 10^4$ | $2.4 \times 10^4$ | $2.0 \times 10^2$ |
| Example for Reference | 0.05% | — | — | $4.0 \times 10^2$ | <2 |
|  | 0.01% | — | — | $4.8 \times 10^4$ | $6.0 \times 10^2$ |

From the test results in Table 3, it is apparent that the anti-bacteria agent made from surf clams achieves a sufficient disinfecting effect even in a further lower concentration thereof, i.e., 0.025%.

Next, the further test of the disinfecting effects is conducted on the anti-bacteria agent made from surf clams according to the present invention (surf clam calcium powder), calcium bicarbonate, scallop shells, clam shells, turban shells, snail shells or oyster shells in Yamagata-ken Rikagaku-Bunseki (physics and chemistry analysis) Center. The results are shown in the following Tables 4 through 16.

TABLE 4

(Sample: Surf clam calcium power (Present Invention))

|  | Number of General bacteria (/ml), Standard agar culture medium method | Group Number of *Esherichia coli*, desoxycol acid salt culture medium method |
|---|---|---|
| Testing Liquid (Miscellaneous drainage of hot spring containing sample 0.1% W/V, sampled after 10 minutes) | 120. | 0. |
| Reference Liquid (Miscellaneous drainage of hot spring) | 11,000. | 410. |

TABLE 5

(Sample: Calcium bicarbonate (Burned at 1,000° C.))

|  | Number of General bacteria (/ml), Standard agar culture medium method | Group Number of *Esherichia coli*, desoxycol acid salt culture medium method |
|---|---|---|
| Testing Liquid (River water containing sample 0.1% W/V, sampled after 10 minutes) | 56. | 0. |
| Reference Liquid (River water) | 17,000. | 57. |

TABLE 6

(Sample: Calcium bicarbonate (Not Burned))

|  | Number of General bacteria (/ml), Standard agar culture medium method | Group Number of *Esherichia coli*, desoxycol acid salt culture medium method |
|---|---|---|
| Testing Liquid (River water containing sample 0.1% W/V, sampled after 10 minutes) | 18,000. | 26. |
| Reference Liquid (River water) | 17,000. | 57. |

TABLE 7

(Sample: Dried scallop)

|  | Number of General bacteria (/ml), Standard agar culture medium method | Group Number of *Esherichia coli*, desoxycol acid salt culture medium method |
|---|---|---|
| Testing Liquid (River water containing sample 0.1% W/V, sampled after 10 minutes) | 720. | 0. |
| Reference Liquid (River water) | 3,100. | 56. |

TABLE 8

(Sample: Non-burned scallop)

|  | Number of General bacteria (/ml), Standard agar culture medium method | Group Number of *Esherichia coli*, desoxycol acid salt culture medium method |
|---|---|---|
| Testing Liquid (River water containing sample 0.1% W/V, sampled after 10 minutes) | 4,100. | 62. |
| Reference Liquid (River water) | 3,100. | 56. |

TABLE 9

(Sample: Dried Clam)

| | Number of General bacteria (/ml), Standard agar culture medium method | Group Number of Esherichia coli, desoxycol acid salt culture medium method |
|---|---|---|
| Testing Liquid (River water containing sample 0.1% W/V, sampled after 10 minutes) | 630. | 0. |
| Reference Liquid (River water) | 3,100. | 56. |

TABLE 10

(Sample: Non-burned Clam)

| | Number of General bacteria (/ml), Standard agar culture medium culture | Group Number of Esherichia coli, desoxycol acid salt culture medium method |
|---|---|---|
| Testing Liquid (River water containing sample 0.1% W/V, sampled after 10 minutes) | 3,700. | 48. |
| Reference Liquid (River water) | 3,100. | 56. |

TABLE 11

(Sample: Dried Turban shell)

| | Number of General bacteria (/ml), Standard agar culture medium method | Group Number of Esherichia coli, desoxycol acid salt culture medium method |
|---|---|---|
| Testing Liquid (River water containing sample 0.1% W/V, sampled after 10 minutes) | 720. | 0. |
| Reference Liquid (River water) | 3,100. | 56. |

TABLE 12

(Sample: Non-burned Turban shell)

| | Number of General bacteria (/ml), Standard agar culture medium method | Group Number of Esherichia coli, desoxycol acid salt culture medium method |
|---|---|---|
| Testing Liquid (River water containing sample 0.1% W/V, sampled after 10 minutes) | 3,700. | 54. |
| Reference Liquid (River water) | 3,100. | 56. |

TABLE 13

(Sample: Dried Snail shell)

| | Number of General bacteria (/ml), Standard agar culture medium method | Group Number of Esherichia coli, desoxycol acid salt culture medium method |
|---|---|---|
| Testing Liquid (River water containing sample 0.1% W/V, sampled after 10 minutes) | 650. | 0. |
| Reference Liquid (River water) | 3,100. | 56. |

TABLE 14

(Sample: Non-burned Snail shell)

| | Number of General bacteria (/ml), Standard agar culture medium method | Group Number of Esherichia coli, desoxycol acid salt culture medium method |
|---|---|---|
| Testing Liquid (River water containing sample 0.1% W/V, sampled after 10 minutes) | 3,600. | 47. |
| Reference Liquid (River water) | 3.100. | 56. |

TABLE 15

(Sample: Dried Oyster shell)

| | Number of General bacteria (/ml), Standard agar culture medium method | Group Number of Esherichia coli, desoxycol acid salt culture medium method |
|---|---|---|
| Testing Liquid (River water containing sample 0.1% W/V, sampled after 10 minutes) | 620. | 0. |
| Reference Liquid (River water) | 3,100. | 56. |

TABLE 16

(Sample: Non-burned Oyster shell)

| | Number of General bacteria (/ml), Standard agar culture medium method | Group Number of Esherichia coli, desoxycol acid salt culture medium method |
|---|---|---|
| Testing Liquid (River water containing sample 0.1% W/V, sampled after 10 minutes) | 3,700. | 62. |
| Reference Liquid (River water) | 3,100. | 56. |

From the above Tables 4 through 16, it is apparent that shell powders of surf clam were inferior to calcium bicarbonate in a disinfecting power or effect; however they were superior to shell powders of other shells. Also, including other shells, it is apparent that a remarkable difference occurs between the burned one and the unburned one in a disinfecting power or effect.

Hereinafter, explanation will be given on embodiments for obtaining freshwater from sea water, for purifying river water, and for washing agricultural products, by referring to FIGS. 1 through 3.

FIG. 1 is a block diagram for obtaining freshwater from sea water. First, sea water is pumped up by means of a pump into a reservoir tank.

Next, at a lower side of the reservoir tank a separation tank is provided, which is divided into the first side chamber and the second side chamber through a reverse permeable membrane, and sea water within the reservoir tank is sent into the first side chamber through a conduit.

A pressure of water head acts on the sea water in the first side chamber, and freshwater is permeated through the reverse permeable membrane into the second side chamber, with being removed NaCl etc. therefrom.

The freshwater in the second side chamber permeates through a column which is filled with the anti-bacteria agent which is obtained by burning shells, such as surf clams or the like, while it is disinfected. Finally, it is supplied to a desired positions or places.

FIG. 2 (A) shows a method for purifying river water, and FIG. 2 (B) shows a perspective view of a net to be provided or positioned on a bed of river. In this embodiment, burned shells of such as surf clams or the like, are filled in the net, and the net is provided or positioned on a bed of river.

In a case of this embodiment, from a view point of maintaining a purification effect for a long time, it is preferable that burned shells are not crushed finely. Since the burned shells come to be porous, the specific surface area thereof is large, therefore, bacteria which decomposes organic matters is easily propagated thereon. When river water comes to be high in the acidity thereof, contents of shells are dissolved into river water, thereby achieving an effect to keep pH of river water constant.

FIG. 3 (A) shows a condition of washing agricultural products, and FIG. 3 (B) shows a rinsing condition after washing. In this embodiment, within a container filled with a synthetic detergent, a basket(s) in which agricultural products are received is (are) dipped. Next, the basket is taken out therefrom, and water which is contacted with the burned shells mentioned above is sprinkled on the agricultural products by means of a shower, thereby removing the synthetic detergent attached to the surface of the agricultural products.

As is fully mentioned above, the anti-bacteria agent according to the present invention, is manufactured by burning shell powders of surf clams etc. in an atmosphere of inactive gas, and it shows a high disinfecting effect or power.

In more detail, it shows a disinfecting effect upon *Esherichia coli*, such as O-157 or the like, food poisoning bacteria, such as *Staphylococcus aureus, Psedomonas aeruginosa*, Eumycetes, salmonella, enteritis vibrio or the like, and further virus, in a low concentration thereof, and it maintains the disinfecting function for a long time.

Further, shell powders of surf clams etc. are a natural material, which mainly contains calcium which is used also as an additives into foods, therefore it is possible to provide an anti-bacteria agent safe for the human body, and it does not contaminate air, waste water and soil, even when it must be processed to be disposed.

Furthermore, with use of the anti-bacteria agent according to the present invention, shells of surf clams etc. can be used effectively for desalination of sea water, purifying river water, or for washing agricultural products, etc., though they are conventionally embarrassing things as a disposal.

What is claimed is:

1. A washing method of agricultural products, comprising the following steps: washing agricultural products, including vegetables and fruits, with a synthetic detergent; and rinsing said agricultural products washed with water which is contacted with an anti-bacteria agent obtained by heating a surf clam in an atmosphere of inactive gas and burning said surf clam at a temperature which finally reaches 700° C.–2,500° C.

2. A method as defined in claim 1, wherein said surf clam is crushed before or after burned.

3. A method as defined in claim 1, wherein said surf clam after crushed has a maximum particle diameter equal to or less than 100 $\mu$m, and has a mean particle diameter from 1 $\mu$m to 50 $\mu$m.

4. A method as defined in claim 1, wherein the anti-bacterial agent includes a powder obtained by crushing charcoal of bamboo.

5. A washing method of agricultural products, comprising the following steps: washing agricultural products, including vegetables and fruits, with a synthetic detergent; and rinsing said agricultural products washed with water which is contacted with an anti-bacteria agent obtained by heating any one of a scallop, a clam, a turban shell and a snail in an atmosphere of inactive gas and burning said any one of a scallop, a clam, a turban shell, and a snail in a temperature which finally reaches 700° C.–2,500° C.

6. A method as defined in claim 5, wherein said any one of a scallop, a clam, a turban shell and a snail is crushed before or after burned.

7. A method as defined in claim 6, wherein said any one of a scallop, a clam, a turban shell and a snail after crushed has a maximum particle diameter equal to or less than 100 $\mu$m, and has a mean particle diameter from 1 $\mu$m to 50 $\mu$m.

8. A method as defined in claim 5, wherein the anti-bacterial agent includes a powder obtained by crushing charcoal of bamboo.

\* \* \* \* \*